United States Patent [19]

Kountis

[11] Patent Number: 5,388,989
[45] Date of Patent: Feb. 14, 1995

[54] OCCLUSAL SCULPTING TOOL

[76] Inventor: Demetrios A. Kountis, 595 Invernes Dr., Akron, Ohio 44313

[21] Appl. No.: 987,633

[22] Filed: Dec. 9, 1992

[51] Int. Cl.$^6$ .......................... A61C 17/00; A61C 3/00
[52] U.S. Cl. ...................... 433/143; 433/141
[58] Field of Search ................... 433/141, 143

[56] References Cited

U.S. PATENT DOCUMENTS

| | | | |
|---|---|---|---|
| D. 249,062 | 8/1978 | Crafoord et al. ............... | 433/141 X |
| 567,589 | 9/1896 | Fredericks ..................... | 433/144 |
| 1,138,355 | 5/1915 | Carr .............................. | 433/143 |
| 1,220,933 | 3/1917 | Bates ............................. | 433/143 |
| 1,369,582 | 2/1921 | Wagner .......................... | 433/142 |
| 1,397,395 | 11/1921 | Bixler ............................ | 433/143 |
| 1,402,525 | 1/1922 | Moseler .......................... | 433/143 |
| 1,446,906 | 2/1923 | Kelsey ............................ | 433/143 |
| 1,491,129 | 4/1924 | Bouyoucoglou ................. | 433/141 |
| 1,503,610 | 8/1924 | Smith ............................. | 433/143 |
| 1,605,321 | 11/1926 | Bates .............................. | 433/143 |
| 1,605,322 | 11/1926 | Bates .............................. | 433/144 |
| 1,663,826 | 3/1928 | Bier ................................ | 433/141 |
| 1,691,786 | 11/1928 | Roth ............................... | 433/143 |
| 1,707,952 | 4/1929 | Schneider . | |
| 1,875,680 | 9/1932 | Van Horn ....................... | 433/144 |
| 2,552,134 | 5/1951 | Berliner ......................... | 433/143 |
| 2,655,726 | 10/1953 | Diener ............................ | 433/144 |
| 3,309,773 | 3/1967 | Weller ............................ | 433/3 |
| 4,060,897 | 12/1977 | Greenstein ..................... | 433/141 |
| 4,167,063 | 9/1979 | Sosnay ........................... | 433/3 |
| 4,270,902 | 6/1981 | Wiland ........................... | 433/141 |
| 4,465,461 | 8/1984 | Schütz ............................ | 433/3 |
| 4,643,676 | 2/1987 | Jansheski ....................... | 433/143 |
| 4,743,198 | 5/1988 | Kennedy ........................ | 433/143 |
| 4,759,713 | 7/1988 | Heiss et al. .................... | 433/141 |
| 4,988,295 | 1/1991 | Kline ............................. | 433/141 |
| 5,004,419 | 4/1991 | Kline ............................. | 433/143 |
| 5,030,091 | 7/1991 | Svanberg ........................ | 433/143 |
| 5,090,907 | 2/1992 | Hewitt et al. .................. | 433/144 |
| 5,127,833 | 7/1992 | Kline ............................. | 433/143 |

OTHER PUBLICATIONS

Suter Dental Manufacturing Co. Catalog, Jan. 1, 1981.

*Primary Examiner*—Gene Mancene
*Assistant Examiner*—Nicholas D. Lucchesi
*Attorney, Agent, or Firm*—Renner, Kenner, Greive, Bobak, Taylor & Weber

[57] ABSTRACT

An occlusal sculpting tool (10) includes a grip portion (11) having a generally central axis and supporting an occlusal sculpting portion (12) at one end thereof. The occlusal sculpting portion (12) has an extension bar (30) affixed at one end thereof to the grip portion (11) and an occlusal tip (31) affixed to the other end of the extension bar (30). The extension bar (30) has a plurality of angles therein such that the occlusal tip (31) is spaced from the grip portion (11) and generally aligned with the generally central axis of the grip portion (11).

14 Claims, 3 Drawing Sheets

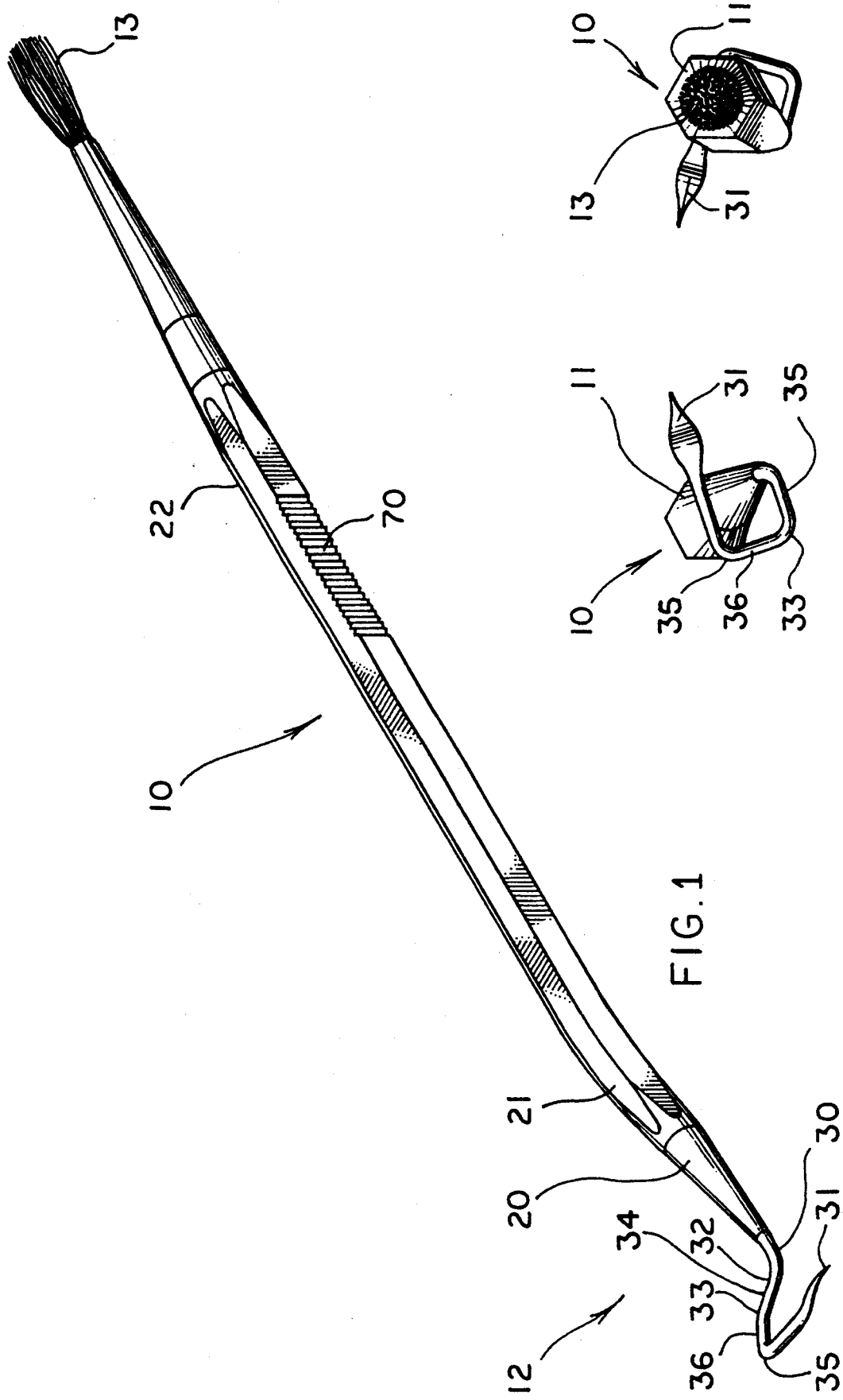

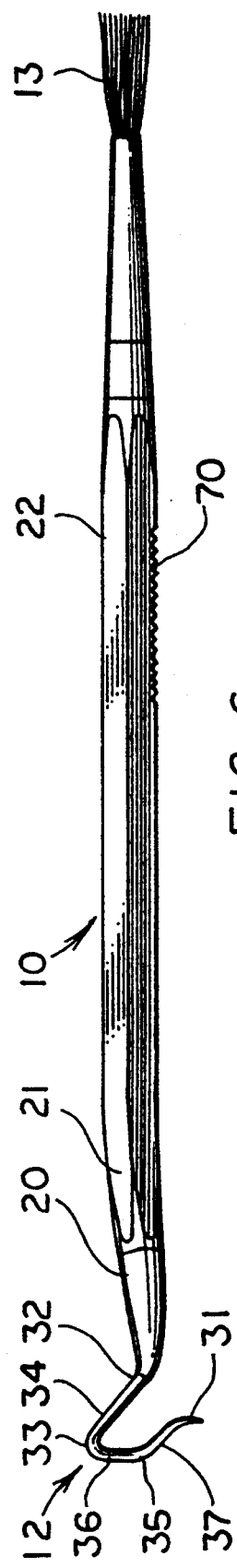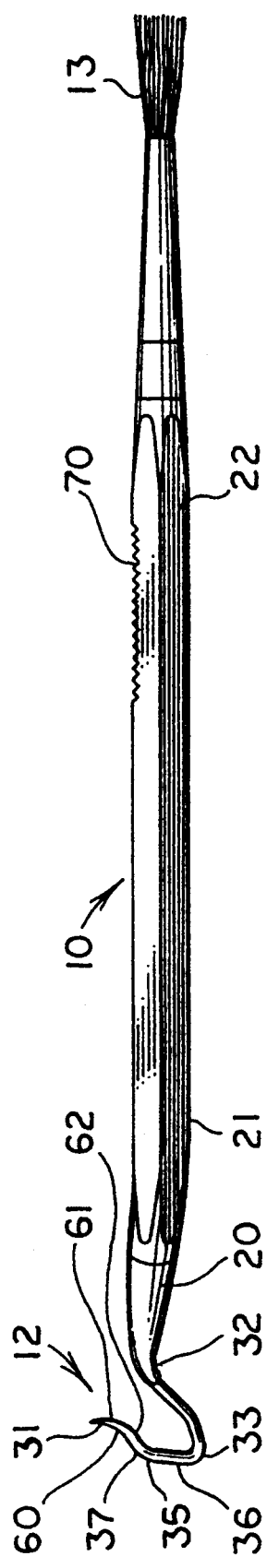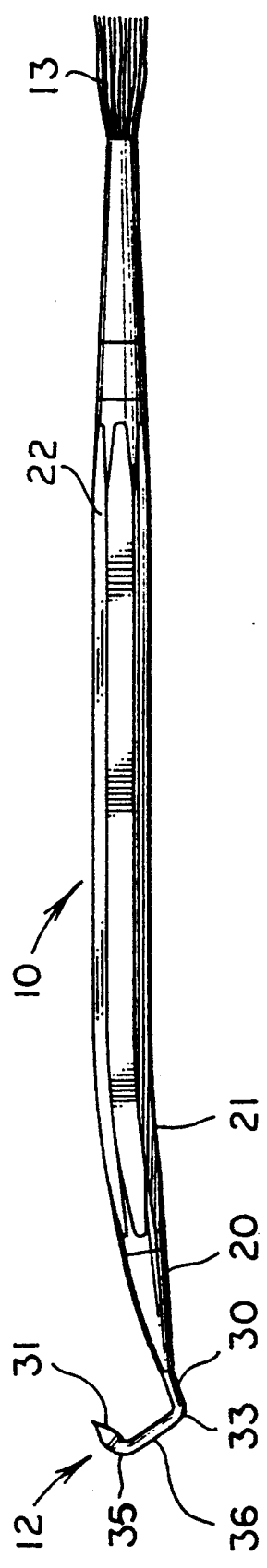

OCCLUSAL SCULPTING TOOL

TECHNICAL FIELD

This invention generally relates to an occlusal sculpting tool for preparing a technical tooth. More particularly, the invention relates to an improved tool for occlusal sculpting. Specifically, the present invention provides an improved occusal sculpting tool having improved user control and which has a tip arrangement allowing for sculpting the emergence profile, the buccal area, the development grooves, the mesio-inciso and disto-inciso areas and all other elements of the occlusal table of a technical tooth.

BACKGROUND OF THE INVENTION

Occlusal sculpting tools are well known in the dental arts. Such tools often include a grip portion affixed to a tip portion, which tip portion is used to sculpt a particular and singular element of the occlusal table. Normally, the dentist or dental technician requires as many as six or more separate tools to sculpt all of the needed occlusal table elements.

It is also known in the art to provide a tip portion extending at an angle from a grip portion of an occlusal tool. For example, U.S. Pat. No. 1,446,906 discloses a dental tool having a tip affixed to a grip portion. The tip extends at an angle to the grip portion.

A need exists for a singular tool which is capable of being manipulated by the user in order to sculpt every element of the occlusal table. The tool should be capable of sculpting the emergence profile, the buccal area, the development grooves, the mesio-inciso and disto-inciso areas and all other elements of the occlusal table of a technical tooth. The present invention provides a singular tool having such capabilities.

SUMMARY OF INVENTION

It is therefore, an object of the present invention to provide an occlusal sculpting tool.

It is another object of the present invention to provide a singular tool as above, which is capable of being employed to sculpt every element of the occlusal table.

It is yet another object of the present invention to provide a tool as above, which provides for improved manipulation by the user, such that occlusal table elements may be efficiently and easily sculpted.

At least one or more of the foregoing objects, together with the advantages thereof over the known art relating to occlusal sculpting tools, which shall become apparent from the specification which follows, are accomplished by the invention as hereinafter described and claimed.

In general the present invention provides an occlusal sculpting tool which comprises a grip portion having a generally central axis and supporting an occlusal sculpting portion at one end thereof. The occlusal sculpting portion has an extension bar affixed at one end thereof to the grip portion, and an occlusal tip affixed to the other end of the extension bar. The extension bar has a plurality of angles therein, such that the occusal tip is spaced from the grip portion and generally aligned with the generally central axis of the grip portion.

BRIEF DESCRIPTION OF THE DRAWINGS

FIG. 1 is a perspective view of an occlusal sculpting tool embodying the concepts of the present invention;

FIG. 2 is an end view of one end of the occlusal sculpting tool of FIG. 1;

FIG. 3 is an end view of the other end of the occlusal sculpting tool of FIG. 1;

FIG. 4 is a side elevational view of the occlusal sculpting tool of FIG. 1;

FIG. 5 is a top plan view of the occlusal sculpting tool of FIG. 1;

FIG. 6 is a bottom plan view of the occlusal sculpting tool of FIG. 1;

PREFERRED EMBODIMENT FOR CARRYING OUT THE INVENTION

Figure 7:
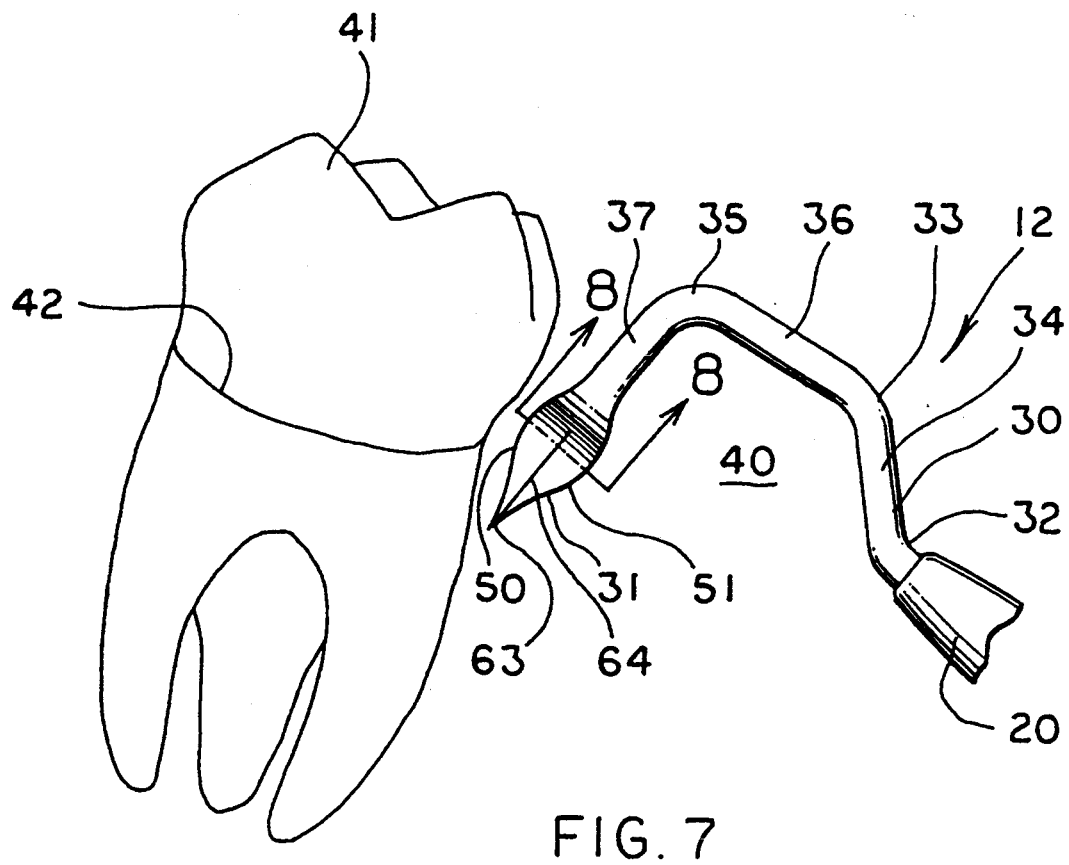
FIG. 7 is an enlarged broken view of one end of the occlusal sculpting tool of FIG. 1, showing the tool in proximity to a tooth for environmental purposes.

An occlusal sculpting tool generally embodying the concepts of the present invention is shown by way of example on the accompanying drawings and is generally designated by the numeral 10 thereon. While occlusal sculpting tool 10 is particularly suited for use in sculpting the occlusal elements of a technical or "false" tooth, it will be appreciated that its use in other dental procedures or even in other arts is equally within the scope of the invention. The present invention will be exemplified hereinbelow with reference to the sculpting of a technical tooth.

Occlusal sculpting tool 10 includes a grip portion 11 and an occlusal sculpting portion generally designated by the numeral 12, at one end thereof. The other end of grip portion 11 may optionally be fitted with a second tool, such as brush 13. Brush 13 is useful in brushing away debris from the tooth being sculpted.

Occlusal sculpting portion 12 and grip portion 11 may be fabricated from a singular material such as a metal or plastic. Preferably however, grip portion 11 is fabricated from a plastic material, and occlusal sculpting portion 12 is fabricated from a metal material. Grip portion 11 may be octagonal in shape, or some other shape, to aid in gripping.

Furthermore, occlusal sculpting portion 12 may be configured to be removably affixable to grip portion 11. While any means of making occlusal sculpting portion 12 removably affixable to grip portion 11, one such means exemplified in the drawings includes cap 20 affixed at one end to grip portion 11 and at the other end to occlusal sculpting portion 12. Cap 20 is preferably removably affixable to grip portion 11 via means such as a friction fit, screw threads (not shown), or the like, and non-removably affixed to said occlusal sculpting portion 12. In order to replace the occlusal sculpting portion 12 of a given occlusal sculpting tool 10, it is merely necessary to remove cap 20 and its affixed occlusal sculpting portion 12 from grip 11 and to replace it with a new cap 20 affixed to a new occlusal sculpting portion 12. This is useful in providing an occlusal sculpting portion 12 configured for variably, a fight and a left-handed user. Furthermore, occlusal sculpting portion 12 may be removed for sterilization purposes and the like.

In order to provide the user of occlusal sculpting tool 10 with a maximum amount of manipulating freedom, and to thus allow the sculpting of every element of the occlusal table, occlusal sculpting tool 10 is provided with a number of angles and sections, as will be discussed hereinbelow.

Grip portion 11 is preferably configured to have a first grip section 21 and a contiguous second grip section 22, angled from first grip section 21. First grip section 21 has a generally central axis, and second grip section 22 has a second generally central axis. The angle between first and second grip sections 21 and 22 may vary, although one preferred angle is about 5 degrees.

Occlusal portion 12 preferably includes an extension bar 30 affixed at one end thereof to grip portion 11, such as via cap 20 as discussed hereinabove, and an occlusal tip 31 affixed to the other end of extension bar 30. Extension bar 30 is provided with a plurality of angles such that occlusal tip 31 is spaced from grip portion 11 and is generally aligned with the generally central axis of first grip section 21, as will be more fully detailed hereinbelow.

Extension bar 30 is preferably angled radially with respect to the generally central axis of first grip section 21, at a first angle 32 (FIG. 7) located proximate to grip 11 or cap 20 if employed. An angle of about 40 degrees is one of many useful angles for first angle 32.

A second angle 33, distal to grip portion 11 is also employed, and a first extension section 34 extends between and connects first and second angles 32 and 33. Similarly, a third angle 35 further distal still to grip portion 11 is present, and a second extension section 36 extends between and connects second angle 33 and third angle 35.

A third extension section 37 extends between and connecting third angle 35 and occlusal sculpting tip 31. Preferably, second extension section 36 extends generally radially with respect to first extension section 34, such that second angle 33 is about 56 degrees. Furthermore, third extension section 37 extends from second extension section 36 such that third angle 35 is about 40 degrees.

By properly selecting the lengths of first, second and third extension sections 34, 36 and 37, and by properly selecting the degrees of angles 32, 33 and 35, which angles may vary from those exemplified hereinabove, an area 40 (FIG. 7) offset from grip portion 11 is formed, such that occlusal tip 31 is spaced from grip portion 11 and is generally aligned with the generally central axis of first grip section 21. Offset area 40 allows the user of occlusal sculpting tool 10 to manipulate occlusal tip 31 to access all areas of a technical tooth, thus allowing the sculpting of every element of an occlusal table, such as for example, the elements of a technical tooth 41 having among other elements, an emergence profile 42, as shown in FIG. 7. The technical tooth will fit within offset area 40 when needed to access certain portions of an occlusal table. The angle between first and second grip sections 21 and 22 also allows more freedom of manipulation for the user of occlusal sculpting tool 10.

In order to sculpt the elements of an occlusal table of technical tooth 4, occlusal tip 31 is generally wedge shaped, as depicted, and is provided with a plurality of sculpting surfaces. Preferably the sculpting surfaces include an outside curve angle 50 and an inside curve angle 51 (FIG. 4). The terms "inside" and "outside" as applied are used in relation to offset area 40. Outside curve angle 50 is useful, for example, in sculpting of the emergence profile 42 of technical tooth 41, and inside curve angle 51 is useful, for example, in sculpting the buccal area and the developmental grooves of technical tooth 41.

By appropriately selecting the widths and lengths of outside curve angle 50 and inside curve angle 51, the depth of the cut which is made when sculpting may be restricted. This provides an improvement over freehand sculpting as has previously been known in the art.

Occlusal tip 31 preferably includes a first flattened section 60 (FIG. 5) extending from and integrally formed with third extension section 37, a second flattened section 61 and an occlusal tip angle section 62 (FIG. 6) extending therebetween. It is also preferred that second flattened section 61 terminates at an end distal to occlusal tip angle section 62, in a point 63 (FIG. 4). Point 63 is useful in sculpting, for example, the mesio-inciso angle and the disto-inciso angle areas of technical tooth 41.

Figure 8:
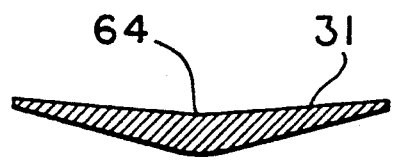
FIG. 8 is an end view of the occlusal sculpting tool taken along lines 8—8 of FIG. 7.

At least one of first or second flattened sections 60 or 61 includes a concave groove 64 therein (FIGS. 7 and 8). Preferably, both first and second flattened sections 60 and 61 include concave groove 64 as depicted in the drawings. Concave groove 64 provides occlusal tip 31 with a spoon-shaped configuration, allowing for efficient sculpting.

Grip portion 11 may be provided with and carry a plurality of spaced, generally parallel ridges 70 (FIGS. 5 and 6). By pulling or dragging an edge (not shown) across ridges 70, water may be purged from the technical tooth being sculpted due to vibrations that result. This allows for improved blotting of the tooth which aids in the reduction of shrinkage thereof.

Thus it should be evident that the device of the present invention is highly effective in providing a singular tool which will allow the user to sculpt every element of an occlusal table, allowing the user to have increased detailing ability. The invention is particularly suited for occlusal sculpting, but is not necessarily limited thereto.

Based upon the foregoing disclosure, it should now be apparent that the use of the occlusal sculpting tool described herein will carry out the objects set forth hereinabove. It is, therefore, to be understood that any variations evident fall within the scope of the claimed invention and thus, the selection of specific component elements can be determined without departing from the spirit of the invention herein disclosed and described.

What is claimed is:

1. An occlusal sculpting tool comprising:

a grip portion having a generally central axis and supporting an occlusal sculpting portion at one end thereof;

said occlusal sculpting portion having an extension bar affixed at one end thereof to said grip portion, and an occlusal tip affixed to the other end of said extension bar;

said extension bar having a plurality of angles therein, such that said occlusal tip is spaced from said grip portion and generally aligned with said generally central axis of said grip portion; wherein said extension bar extends generally radially from said grip portion at a first angle proximate to said grip portion, and has a second angle distal to said grip portion, such that said first and second angles of said extension bar are in different planes; said extension bar also having a first extension section extending between and connecting said first angle and said second angle, a third angle distal to said grip portion, a second extension section extending between and connecting said second angle and said third angle, and a third extension section extending between and connecting said third angle and said occlusal tip.

2. An occlusal sculpting tool, as set forth in claim 1, wherein said first angle is about 40 degrees relative to said generally central axis.

3. An occlusal sculpting tool, as set forth in claim 1, wherein said second extension portion extends generally radially with respect to said first extension section.

4. An occlusal sculpting tool, as set forth in claim 3, wherein said second angle is approximately 56 degrees.

5. An occlusal sculpting tool, as set forth in claim 1, wherein said third angle is approximately 40 degrees.

6. An occlusal sculpting tool, as set forth in claim 1, wherein said grip portion has a first grip section angled from a contiguous second grip section, such that said grip portion has a first and a second generally central axis, and such that said occlusal tip is generally aligned with said generally central axis of said first grip section.

7. An occlusal sculpting tool, as set forth in claim 6, wherein said first grip section is angled from said second grip section by about five degrees.

8. An occlusal sculpting tool, as set forth in claim 1, wherein said grip portion has a brush at the other end thereof.

9. An occlusal sculpting tool, as set forth in claim 1, wherein said grip portion carries a plurality of spaced, generally parallel ridges therein.

10. An occlusal sculpting tool, as set forth in claim 1, wherein said occlusal tip comprises a plurality of sculpting surfaces.

11. An occlusal sculpting tool, as set forth in claim 10, wherein said occlusal tip is generally wedge shaped such that said sculpting surfaces include an outside curve angle and an inside curve angle.

12. An occlusal sculpting tool, as set forth in claim 1, wherein said occlusal tip includes a first flattened section extending from said extension bar, a second flattened section and an occlusal tip angle section therebetween.

13. An occlusal sculpting tool, as set forth in claim 12, wherein said second flattened section terminates at an end distal to said occlusal tip angle section, in a point.

14. An occlusal sculpting tool, as set forth in claim 12, wherein at least one of said first and second flattened sections includes a concave groove therein.

* * * * *